United States Patent [19]

Clarke et al.

[11] Patent Number: 4,734,269
[45] Date of Patent: Mar. 29, 1988

[54] VENOUS RESERVOIR BAG WITH INTEGRAL HIGH-EFFICIENCY BUBBLE REMOVAL SYSTEM

[75] Inventors: Rolf W. Clarke, Balboa Island; David P. Balding, Mission Viejo; Lucas S. Gordon, Lagune Beach, all of Calif.

[73] Assignee: American Hospital Supply Corporation, Evanston, Ill.

[21] Appl. No.: 743,693

[22] Filed: Jun. 11, 1985

[51] Int. Cl.⁴ ............ A61M 1/00; A61M 1/14; A61M 1/34; B01D 19/00
[52] U.S. Cl. ............ 422/310; 422/47; 422/48; 422/231; 128/DIG. 3; 55/159; 261/DIG. 28; 210/131; 210/188; 210/196; 210/356; 210/422; 210/436; 210/927; 604/4; 604/122; 604/126; 604/405
[58] Field of Search ............ 422/310, 47, 45, 44, 422/48, 230, 231; 604/122, 126, 4, 405, 406; 128/DIG. 3; 55/159; 210/436, 472, 927, 99, 131, 188, 196, 354, 356, 405, 420, 422; 261/DIG. 28

[56] References Cited

U.S. PATENT DOCUMENTS

| | | | |
|---|---|---|---|
| 2,828,863 | 4/1958 | Van Lier et al. | 210/131 |
| 3,127,255 | 3/1964 | Winslow | 210/188 |
| 3,509,932 | 5/1970 | Chambers | 159/2 |
| 3,729,377 | 4/1973 | Leonard | 261/DIG. 28 |
| 3,915,650 | 10/1975 | Talonn et al. | 261/DIG. 28 |
| 3,976,452 | 8/1976 | Meier et al. | 55/192 |
| 4,035,304 | 7/1977 | Watanabe | 210/317 |
| 4,046,696 | 9/1977 | Mouwen | 210/927 |
| 4,344,777 | 8/1982 | Siposs | 55/178 |
| 4,345,919 | 8/1982 | Wilkinson et al. | 55/41 |
| 4,428,743 | 1/1984 | Heck | 604/4 |
| 4,493,705 | 11/1985 | Gordon et al. | 604/122 |
| 4,498,990 | 2/1985 | Shaldon et al. | 210/637 |

Primary Examiner—Barry S. Richman
Assistant Examiner—Lynn M. Kummert
Attorney, Agent, or Firm—Gordon L. Peterson

[57] ABSTRACT

A liquid-gas bubble separator comrising a container having an inlet for a fluid which includes liquid and gas bubbles, an outlet and upstream and downstream vents. A filter element is provided in the container between the inlet and the outlet. The filter element permits the passage of the liquid and inhibits the passage of the gas bubbles. The filter element is between the upstream and downstream vents so that gas bubbles which do not pass through the filter element can be vented through the upstream vent, and any gas bubbles downstream of the filter element can be vented through the downstream vent. A bypass passage is provided around the filter element. A portion of the filtered fluid is recirculated through the bypass passage to prevent forward flow through the bypass passage when the filter element is clean, and such recirculating flow is terminated when the filter is clogged to a predetermined degree to thereby open the bypass passage for forward flow.

24 Claims, 7 Drawing Figures

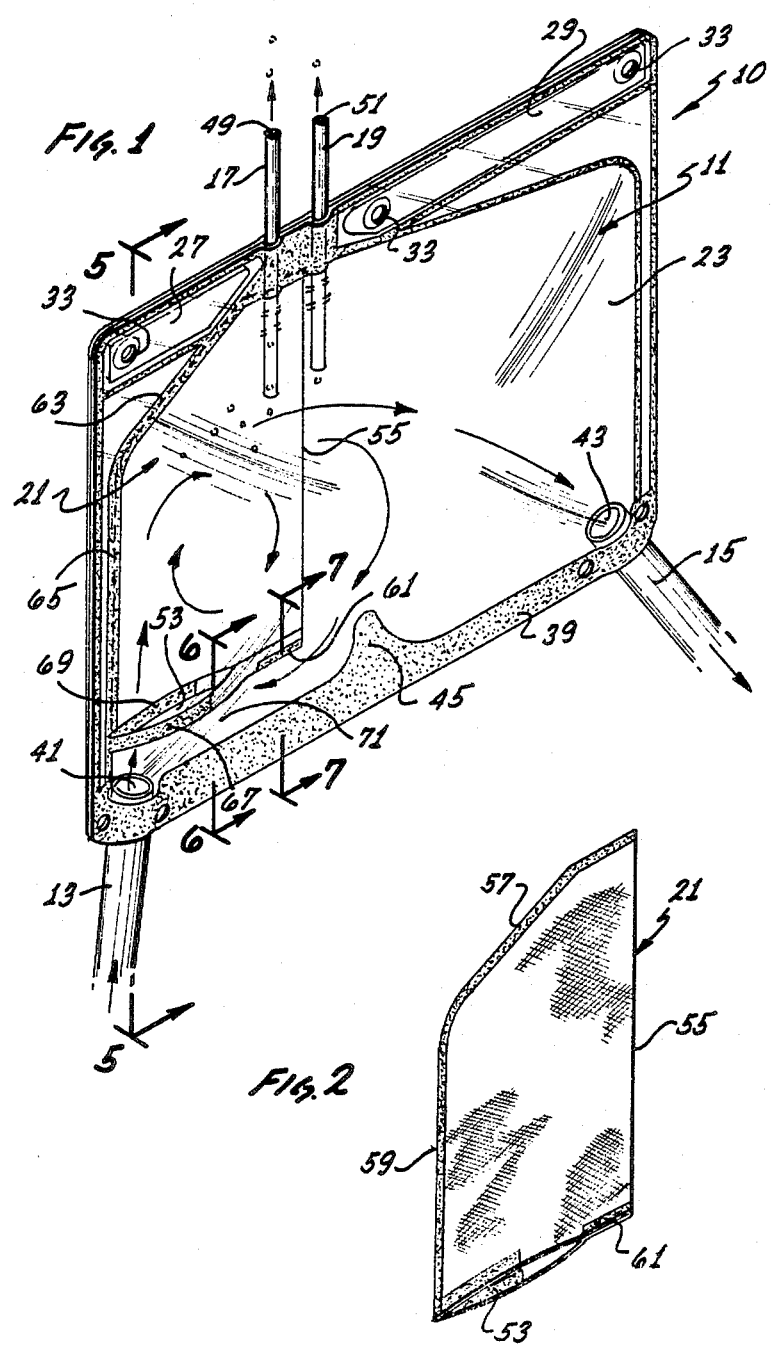

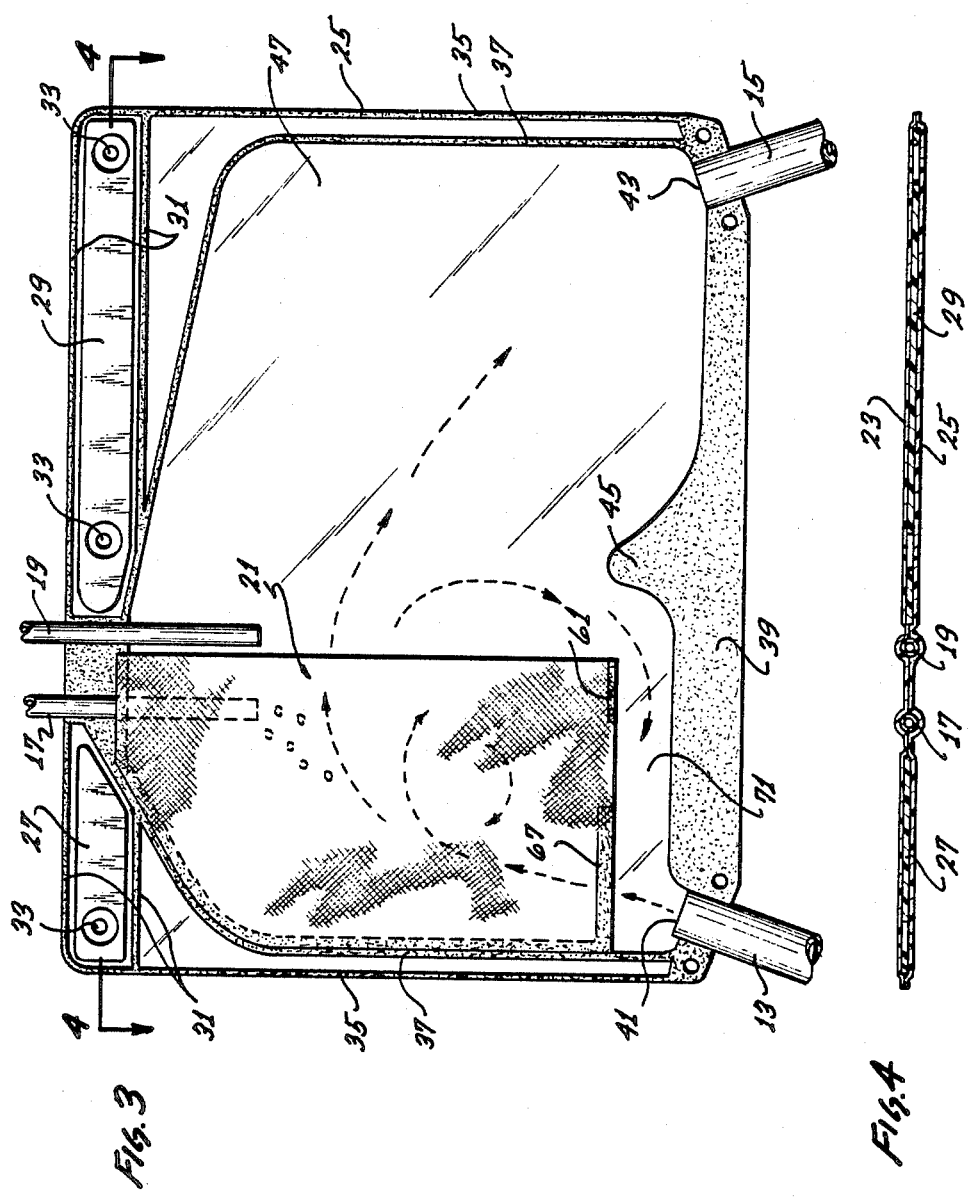

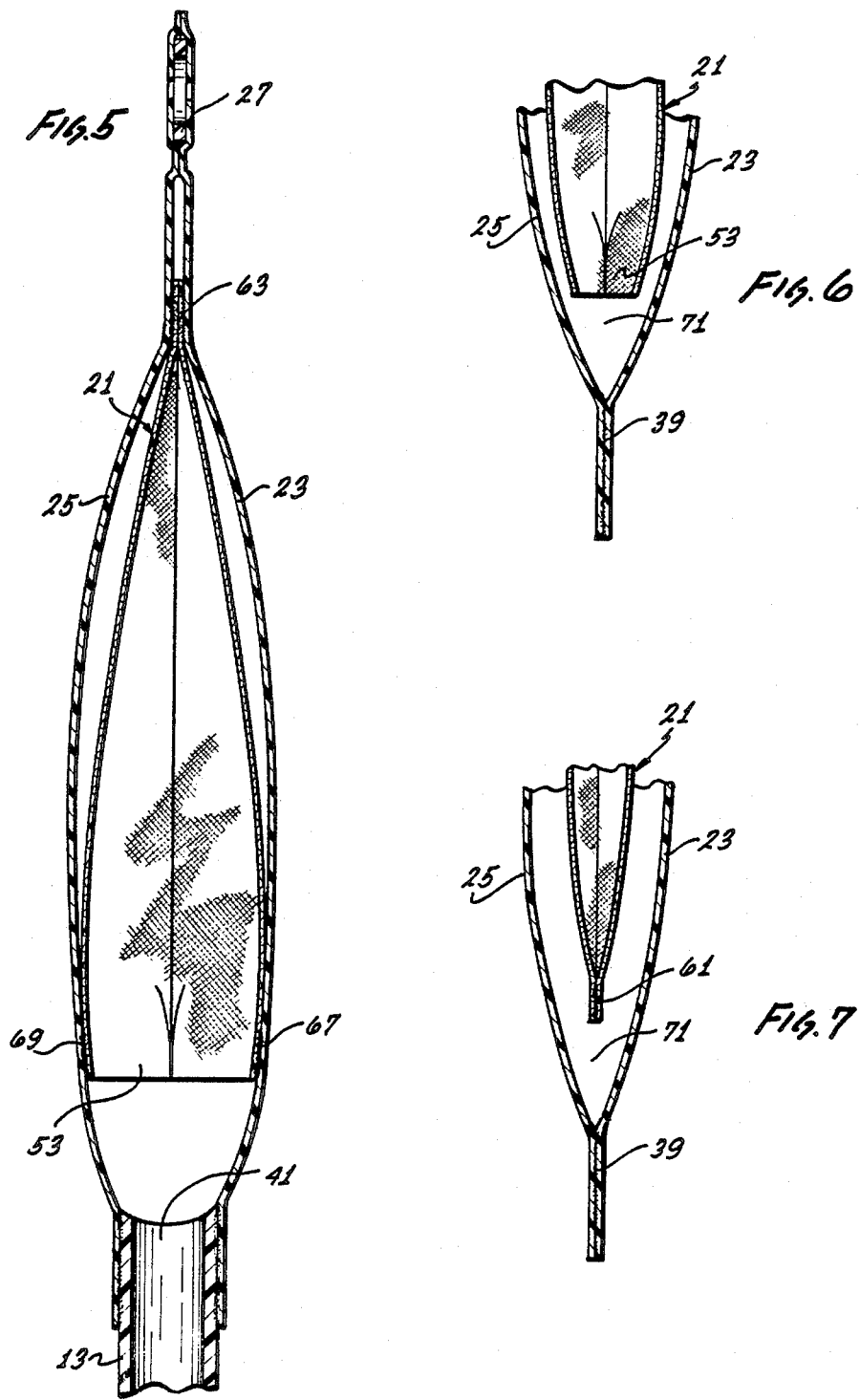

VENOUS RESERVOIR BAG WITH INTEGRAL HIGH-EFFICIENCY BUBBLE REMOVAL SYSTEM

BACKGROUND OF THE INVENTION

A venous reservoir bag is commonly used in a cardiopulmonary bypass loop. A reservoir bag provides an accumulator function in that it allows for variations in blood volume when cardiopulmonary bypass is conducted with a membrane oxygenator. In addition, the reservoir bag separates bubbles from the venous blood or prime solution circulated in the bypass loop and vents the gas to atmosphere. Gas bubbles may enter the cardiopulmonary loop as a result of air or other gases being in the lines before priming or being entrapped in the venous blood at the operating site.

One prior art reservoir bag has a blood inlet and a blood outlet along the lower edge of the bag and an air vent at the top of the bag. As blood flows through the bag from the inlet to the outlet, gas bubbles rise and are vented through the vent. Unfortunately, prior art bags of this type do not remove all of the gas bubbles from the blood, particularly when blood flow rates are high, the gas bubbles are relatively small and there is a low liquid volume in the bag. Although the oxygenator will remove some of the gas bubbles, the primary gas removal occurs in the venous reservoir bag. It is important that all of the gas be removed because gas emboli in the cardiovascular system of the patient can be fatal.

Siposs U.S. Pat. No. 4,344,777 shows a bubble trap for arterial blood in which a filter element is used to assist in the separation of the gas bubbles from the blood. Although a porous filter element can be quite effective in this separation function, there is a danger that the filter element can become plugged, in which event, blood flow to the patient would be terminated. In an attempt to deal with the clogging problem, the patentee provides a bypass outlet for use in those cases where the filter element is plugged up but system flow must continue. The bypass outlet is connected by a flexible tube to the regular outlet tube, and a clamp normally closes the bypass outlet. This requires that the attendant immediately observe the clogged condition of the filter element and manually open the clamp in order to prevent blood flow back to the patient.

It is also known to provide an elastic, pressure-sensitive valve between an inlet and one outlet of a filter so that undesired pressure buildup at the inlet results in at least some of the liquid to be filtered passing from the inlet directly to the outlet. This filter, which is shown in Shaldon et al U.S. Pat. No. 4,498,990, does not remove gas emboli from blood.

SUMMARY OF THE INVENTION

This invention solves these problems and provides a number of other significant advantages. With this invention, a filter element is used to assist in separation of the liquid and gas bubbles, and a bypass passage is provided around the filter element for bypassing the liquid around the filter element when the latter is at least partly clogged. However, unlike the prior art, the bypass passage is normally closed for forward flow by recirculating a portion of the filtered fluid back through the bypass package. Whenthe filter element becomes clogged to a predetermined degree, such recirculation of filtered fluid is essentially terminated so that forward flow through the bypass passage and around the filter element can occur. Thus, this invention uses a portion of the filtered fluid to automatically control the effective opening and closing of the bypass passage.

This produces significant advantages. For example, no mechanical bypass valve is required, and consequently, there are no mechanical valve components which can stick, leak, or otherwise fail to function properly. As a result, reliability is increased, assembly is facilitated, and cost is reduced. In addition, the recirculating of the filtered fluid provides a second stage filtering action for the recirculated fluid to further assure the absence of any gas bubbles from the liquid discharged from the container.

Another important advantage of this invention is that no separate pressure sensors are required for sensing when the filter element is clogged. In this regard, the recirculation of the filtered fluid responds automatically to a predetermined pressure drop across the filter element to allow at least some forward flow of unfiltered liquid through the bypass passage. Thus, reduction of the percent of open area through the filter element automatically opens the bypass passage for forward flow.

The invention is particularly adapted to separate gas bubbles from liquid in a medical fluid, such as blood or a priming solution. However, the invention is more broadly adapted to carry out liquid-gas bubble separation of fluids generally.

The invention can be implemented in different ways. For example, the invention may be in the form of a liquid-gas bubble separator which preferably comprises a container having an inlet, an outlet, and a flow channel extending between the inlet and the outlet and a filter element extending from one side of the flow channel only part way across the flow channel to thereby define a bypass passage in the flow channel which bypasses the filter element. The filter element permits the passage of the liquid and inhibits the passage of gas bubbles. An upstream vent leads from the upstream side of the filter element to the exterior of the container so that the separated gas bubbles can be vented from the container.

When the above-described preferred liquid-gas separator construction is employed, the bypass passage may be open at all times or have flow therethrough controlled by a conventional valve. However, preferably the flow of fluid through the bypass passage is controlled by means for recirculating a portion of the filtered fluid that passes through the filter element through the bypass passage to the upstream side of the filter element, at least when the filter element is clean. The recirculating means serves like valve means for opening and closing the bypass passage.

Recirculation of filtered fluid through the bypass passage can be accomplished in different ways. For example, a swirling or vortex-like flow can be provided in the liquid upstream of the filter element. The swirling flow can be induced in any suitable way, such as by directing the incoming fluid stream along the surface of the filter element rather than directly against the filter element at a 90-degree angle.

Recirculation can also be provided or assisted by directing incoming fluid in a direction extending generally across the bypass passage and into the flow channel on the upstream side of the filter media. This tends to induce a lower pressure at the upstream end of the bypass passage to help draw filtered liquid through the bypass passage in the reverse direction. When the filter becomes clogged to a predetermined degree, forward flow of unfiltered fluid through the bypass passage is forced to occur due to the higher resistance to flow through the filter element.

To provide for separation of the gas bubbles from the liquid downstream of the filter element in a clogged filter element condition, a downstream vent is provided which leads from the downstream side of the filter element to the exterior of the container. This also provides for a second-stage venting of any gas bubbles that may exist downstream of the filter element when the filter element is unclogged. This two-stage venting feature of this invention can be provided if the valve means for opening and closing the bypass passage is mechanical or provided in accordance with other features of this invention or if no valve is provided for the bypass passage.

Although the filter element can take different forms, in a preferred construction, it includes a generally tubular filter element having an opening at one end facing the bypass passage and the inlet, and the upstream vent extends into the tubular filter element. Although the filter element can be of different types and materials, it can advantageously take the form of a porous filter screen. To aid in forming the vortex-like flow, a portion of the end of the tubular filter element containing the opening is closed.

The container can be rigid or flexible and in virtually any configuration, including a bag, pipe-like conduit, etc. The tubular filter element can be joined to the container along the opposite sides of the opening in the tubular filter element. With this arrangement, if the container is flexible, the bag expands as it is filled, and the opening of the tubular filter element is pulled open to insure that none of the liquid can escape without passing through the filter element so long as the filter element is unclogged.

Forward flow from the bypass passage is preferably directed toward the downstream vent to give any gas bubbles ample opportunity to be vented. In this regard, the blood inlet and blood outlet can advantageously be located along the lower side of the flow channel, and the vents preferably lead from the upper side of the flow channel.

The invention, together with additional features and advantages thereof, may best be understood by reference to the following description taken in connection with the accompanying illustrative drawing.

BRIEF DESCRIPTION OF THE DRAWING

FIG. 1 is an isometric view of a venous reservoir bag constructed in accordance with the teachings of this invention.

FIG. 2 is an isometric view of one form of filter element.

FIG. 3 is a front elevational view of the venous reservoir bag, with the front layer of the bag removed.

FIG. 4 is a sectional view taken generally along line 4—4 of FIG. 3.

FIGS. 5-7 are sectional views taken generally along lines 5—5, 6—6 and 7—7, respectively, of FIG. 1.

DESCRIPTION OF THE PREFERRED EMBODIMENT

FIG. 1 shows a liquid-gas separator in the form of a venous reservoir bag 10 which comprises a container 11, an inlet tube 13, an outlet tube 15, an upstream vent tube 17, a downstream vent tube 19 and filter element 21. Although the container 11 may be rigid, in this embodiment, it is in the form of a flexible transparent bag, and it comprises two layers 23 and 25 (FIG. 5) of a suitable biocompatible plastic material heat sealed together along their peripheral edges. To facilitate hanging of the container 11 from a suitable support, such as an IV pole, tear resistant strips 27 and 29 (FIGS. 1, 3 and 4) are held captive in elongated slots formed between the layers 23 and 25 by heat seals 31 (FIG. 3) between such layers. The layers 23 and 25 and the strips 27 and 29 have openings 33 from which the container can be suspended.

As best shown in FIG. 3, the layers 23 and 25 are heat sealed together by a double heat seal 35 and 37 along their opposite side edges and are heat sealed together by a relatively wide heat seal 39 along their lower edges. The heat seal 39 is interrupted at its opposite ends at the lower corners of the container 11 by the inlet tube 13 and the outlet tube 15 which define an inlet 41 and an outlet 43, respectively, for the venous reservoir bag 10. The heat seal 39 is thickened intermediate its ends to form a ridge 45 (FIG. 3) for a purpose described hereinbelow. The container 11 has a flow channel 47 extending between the inlet 41 and the outlet 43. The vent tubes 17 and 19 lead from the flow channel 47 through the heat seals 31 along the upper edge of the container 11 and define upstream and downstream vents 49 and 51, respectively. The inlet tube 13, the outlet tube 15 and the vent tubes 17 and 19 can be mounted on the container 11 in any suitable manner, such as by an adhesive.

Although various different kinds of filter elements 21 can be used, in the embodiment illustrated, the filter element is in the form of a porous filter screen having a pore size of between 50 and 300 microns. The filter screen may be constructed of, for example, plain weave or twill weave nylon or polyester material having 50 percent open area or a depth filter material. Single or multiple layers of the filter screen can be employed. The filter screen is preferably coated with a blood compatible coating, such as heparin. The filter screen will separate gas bubbles, such as air bubbles, from blood, but will not separate the dissolved blood gases from the blood.

Although the filter element 21 can be arranged in various different geometric configurations, it is preferably tubular as shown in FIG. 2. The filter element 21 has an opening 53 at its lower end. To form the tubular configuration, the filter screen material is folded along a side edge 55 (FIG. 2) and then heat sealed together along the full length of its upper edge 57 and of the opposite side edge 59. A portion of the bottom edge of the filter element adjacent the edge 55 is closed by a heat seal 61. The opening 53 extends from the edge 59 to the heat seal 61 and, in this embodiment, is longer than the heat seal 61.

Although the filter element 21 can be mounted in the flow channel 47 in various different ways, in the embodiment illustrated, it is heat sealed to the container 11 by a heat seal 63 (FIG. 1) extending along the top edge of the filter element and a heat seal 65 extending along the left edge of the filter element as viewed in FIG. 1. Heat seals 67 and 69 (FIGS. 1 and 5) which extend from the edge 59 of the filter element along a major length of the opening 53 join the opposite sides of the opening 53 of the filter element to the layers 23 and 25. Because the filter element 21 is heat sealed to the container 11 along the heat seals 67 and 69, inflation of the container with a fluid enlarges the opening 53 as shown in FIG. 5.

With the filter element 21 mounted in the flow channel 47 in this manner, the filter element extends from the top of the flow channel only part way across the flow channel to define a bypass passage 71 (FIGS. 1, 3, 6 and 7) which bypasses the filter element in extending from the upstream side of the filter element to the downstream side thereof. The bypass passage 71 is directed upwardly generally toward the vent 51 by the ridge 45 so that flow exiting the bypass passage downstream of the filter element 21 is directed generally toward the downstream vent. The opening 53 faces the bypass passage 71 and the inlet 41. The upstream vent 49 extends into the tubular filter element 21, and the downstream vent 51 is downstream of the filter element.

In use, the reservoir bag 10 is adapted to be connected into an extracorporeal circuit during cardiopulmonary bypass surgery. When coupled in this circuit, the venous reservoir bag 10 receives blood from the patient through the inlet tube 13. The inlet tube 13 directs the incoming blood through the inlet 41 in a direction extending generally across the bypass passage 71 and into the flow channel 47 on the upstream side of the filter element 21. More particularly, blood flow is directed through the opening 53 into the interior of the tubular filter element 21. This tends to create a slight negative pressure in the bypass passage 71 near the inlet 41. The flow is directed generally upwardly such that it is generally along the interior surface of the filter element 21 rather than being directed transversely through the filter element. As blood volume within the container 11 expands the container, the heat seals 67 and 69 progressively open the opening 53 to assure that the incoming blood stream will enter the tubular filter element 21.

Blood flow within the container 11 is generally toward the upstream vent 49, and any gas bubbles within the blood tend to rise toward the upstream vent and be vented to atmosphere. The filter element 21 permits the passage of the blood and inhibits the passage of gas bubbles, and this further tends to separate the gas bubbles from the blood and allow the gas to pass out of the container 11 through the upstream vent 49.

The blood that passes through the filter element 21, which may be considered as filtered blood, flows toward the outlet 43, and if any gas bubbles are present, they tend to rise to the surface and be vented through the downstream vent 51 which provides, in effect, a second-stage vent.

Some of the blood within the tubular filter element 21 does not immediately pass through the filter element but rather is directed down along the edge 55 within the tubular filter element toward the heat seal 61. The heat seal 61 redirects this flow toward the incoming flow at the opening 53. This creates a swirl or vortex-like flow within the tubular filter element 21 which combines with the negative pressure in the bypass passage 71 resulting from the incoming flow from the inlet 41 to draw in a small percent of the filtered blood from downstream of the filter element 21 through the bypass passage 71. Thus, with the filter element 21 unclogged, flow through the bypass passage 71 is in the reverse direction, i.e., from downstream of the filter element 21 toward the upstream side of the filter element as shown by the arrows in FIG. 1. This serves as a valve to close the bypass passage 71 for forward flow, i.e., from upstream of the filter element 21 to downstream of the filter element 21 or as recirculating means for recirculating a portion of the filtered blood. The recirculation of some of the filtered blood, not only closes the bypass passage 71, but also provides for passing a mixture of filtered and unfiltered blood through the filter element 21 to further assure elimination of all gas bubbles from the blood returning to the patient.

If the filter element 21 becomes clogged to a certain degree, the recirculation of filtered blood through the bypass passage 71 terminates due to the tendency of the blood to take the path of least resistance so that some blood flow through the bypass passage in the forward direction occurs. Of course, at some greater degree of clogging of the filter element 21, all of the incoming blood from the inlet 41 flows through the bypass passage 71 into the flow channel 47 downstream of the filter element. The ridge 45 directs the flow exiting the bypass passage 71 generally toward the downstream vent 51 so that gas bubbles can separate from the blood and be vented through the downstream vent.

The bypass passage 71 opens for forward flow when the resistance to flow through the filter element reaches a certain magnitude. Although this increased resistance to flow will ordinarily be brought about by clogging of the filter, under certain conditions, it may be brought about by a high volume of gas bubbles in the container 11 which would reduce the open area of the filter available for the passage of liquid.

Although an exemplary embodiment of the invention has been shown and described, many changes, modifications and substitutions may be made by one having ordinary skill in the art without necessarily departing from the spirit and scope of this invention.

We claim:

1. A liquid-gas bubble separator comprising:
    a container having an inlet, an outlet, and a flow channel extending between the inlet and the outlet;
    a filter element extending from one side of the flow channel only part way across the flow channel to define a bypass passage in the flow channel which bypasses the filter element, said filter element permitting the passage of liquid and inhibiting the passage of gas bubbles;
    said filter element dividing said flow channel into an upstream portion and a downstream portion, said upstream portion being located between said inlet and said filter element and said downstream portion being located between said filter element and said outlet;
    said filter element being positioned and arranged in said container so as to define a flow passage around said filter element leading from the upstream portion to the downstream portion, said bypass passage being open to fluid flow in both directions;
    said filter element being constructed and arranged so as to provide a slight negative pressure in said bypass passage and a vortex-like flow within said filter element when liquid flows therethrough so as to recirculate some of a liquid which has passed through said filter element back to said upstream portion of said flow channel when the filter element is substantially clean to essentially close the bypass passage to flow therethrough directly from said upstream portion to said downstream portion; and
    a first vent leading from the upstream portion to the exterior of the container.

2. A liquid-gas bubble separator comprising:

a container having an inlet for a fluid which includes liquid and gas bubbles, an outlet and a flow channel extending between said inlet and said outlet;

a filter element in said container positioned in said flow channel between said inlet and said outlet and dividing said flow channel into an upstream portion and a downstream portion, said upstream portion being located between said inlet and said filter element and said downstream portion being located between said filter element and said outlet, said filter element permitting the passage of liquid and inhibiting the passage of gas bubbles;

an upstream vent located in said upstream portion and a downstream vent located in said downstream portion;

said filter element being between the upstream vent and the downstream vent whereby gas bubbles that do not pass through said filter element can be vented through the upstream vent and any gas bubbles downstream of the filter element can be vented through the downstream vent;

said filter element being positioned and arranged in said container so as to define a bypass passage around said filter element leading from the upstream portion to the downstream portion, said bypass passage being open to fluid flow in both directions; and said filter element being constructed and arranged so as to provide a slight negative pressure in said bypass passage and a vortex-like flow within said filter element when liquid flows therethrough so as to recirculate some of a liquid which has passed through said filter element back to said upstream portion of said flow channel when the filter element is substantially clean to essentially close the bypass passage to flow therethrough directly from said upstream portion to said downstream portion.

3. A liquid-gas bubble separator comprising:
a container having an inlet for a fluid which includes liquid and a gas, an outlet and upstream and downstream vents;

a filter element in said container between the inlet and the outlet, said filter element having upstream and downstream sides and permitting the passage of the liquid and inhibiting the passage of the gas bubbles;

said filter element being between the upstream vent and the downstream vent whereby gas bubbles that do not pass through said filter element can be vented through the upstream vent and any gas bubbles downstream of the filter element can be vented through the downstream vent;

a bypass passage around said filter element leading from the upstream side of the filter element to the downstream side thereof, said bypass passage being open to fluid flow in both directions when liquid is not flowing through the container; and first means for controlling the direction of passage of liquid through the bypass passage, said first means including means for directing some of the liquid which passes through the filter element through said bypass passage from the downstream side of the filter element to the upstream side of the filter element at least when the filter element is clean to essentially close the bypass passage to flow therethrough from the upstream side of the filter element to the downstream side of the filter element.

4. A separator as defined in claim 3 wherein said first means is responsive to the differential pressure across said filter element reaching a predetermined magnitude to open the bypass passage.

5. A separator as defined in claim 3 including means for directing flow exiting the bypass passage on the downstream side of the filter element generally toward the downstream vent.

6. A separator as defined in claim 3 wherein said first means is responsive to at least some clogging of the filter element to decrease the flow of liquid through the bypass passage from the downstream side of the filter element to the upstream side of the filter element.

7. A liquid-gas bubble separator comprising:
a container having an inlet, an outlet, and a flow channel extending between the inlet and the outlet;

a filter element extending from one side of the flow channel only part way across the flow channel to define a bypass passage in the flow channel which bypasses the filter element, said filter element permitting the passage of liquid and inhibiting the passage of gas bubbles;

recirculating means responsive to flow through the container when the filter element is clean for recirculating a portion of the fluid that passes through said filter element through the bypass passage in one direction so that said portion of the fluid can pass through the filter element again and the bypass passage is essentially closed by said portion of fluid to flow therethrough in a direction opposite to said one direction; and a first vent leading from the flow channel to the exterior of the container and being positioned and arranged to vent gas bubbles which do not pass through said filter element.

8. A separator as defined in claim 7 wherein said recirculating means is constructed and arranged to terminate recirculation in response to a differential pressure across the filter element reaching about a predetermined magnitude.

9. A separator as defined in claim 7 wherein said recirculating means includes means for creating a swirling flow on the upstream side of the filter element to at least assist in inducing recirculating flow through the bypass passage.

10. A separator as defined in claim 7 wherein said flow channel has upper and lower sides, said one side of said flow channel is the upper side, and said inlet and said outlet and the bypass passage are along the lower side of the flow channel and said first vent is at the upper side of the flow channel.

11. A separator as defined in claim 7 wherein said recirculating means includes the inlet being arranged to direct incoming fluid in a direction which extends generally across the bypass passage and into the flow channel on the upstream side of the filter element.

12. A separator as defined in claim 11 wherein said filter element includes a generally tubular filter element having an opening at one end facing said bypass passage and said inlet and said first vent extend into said tubular filter element.

13. A separator as defined in claim 7 including a second vent leading from the flow channel between the filter element and the outlet to the exterior of the container.

14. A separator as defined in claim 13 wherein said container is flexible, said flow channel has upper and lower sides, said first side of the flow channel is the upper side, said inlet and said outlet and the bypass passage are along the lower side of the flow channel, said vents are at the upper side of the flow channel, and means for directing flow exiting the bypass passage downstream of the filter element generally toward the second vent.

15. A separator as defined in claim 14 wherein said filter element includes a generally tubular filter element having an opening at its lower end, said opening faces said bypass passage and said inlet and said first vent extends into the tubular filter element.

16. A liquid-gas bubble separator comprising:
a reservoir bag having an inlet, an outlet, and a flow channel extending between the inlet and the outlet;
a filter element extending from one side of the flow channel only part way across the flow channel to define a bypass passage in the flow channel which bypasses the filter element, said filter element permitting the passage of the liquid and inhibiting the passage of the gas bubbles;
said inlet directing incoming fluid into the flow channel on the upstream side of the filter element;
a first vent leading from the flow channel to the exterior of the reservoir bag and being positioned and arranged to vent gas bubbles which do not pass through the filter element; and
said bypass passage being open to flow in both directions when liquid is not flowing through the reservoir bag.

17. A separator as defined in claim 16 wherein the inlet is positioned and arranged to direct incoming fluid in a direction extending generally across the bypass passage.

18. A separator as defined in claim 16 including a second vent leading from the flow channel to the exterior of the reservoir bag and being positioned and arranged to vent gas bubbles which pass through the filter element.

19. A separator as defined in claim 18 wherein said flow channel has upper and lower sides, said one side of the flow channel is the upper side, said inlet and outlet and bypass passage are along the lower side of the flow channel and said vents are at the upper side of the flow channel.

20. A separator as defined in claim 18 wherein said filter element includes a generally tubular filter element having an opening at one end facing said bypass passage and said inlet, said first vent extending into the tubular filter element.

21. A separator as defined in claim 20 wherein the inlet is positioned and arranged to direct incoming fluid in a direction extending generally across the bypass passage.

22. A separator as defined in claim 20 wherein a portion of said one end of the tubular filter element adjacent the opening is closed.

23. A separator as defined in claim 20 wherein the flow channel has upper and lower sides and upstream and downstream ends and said tubular filter element is joined to the upper side and to the upstream end of the flow channel and said opening of said filter element opens downwardly toward the inlet and the bypass passage.

24. A separator as defined in claim 20 wherein the tubular filter element is joined to the bag on the opposite sides of the opening so that inflation of the bag with liquid pulls the opening of the filter element open.

* * * * *